(12) United States Patent
Skigen (10) Patent No.: US 9,693,969 B2
(45) Date of Patent: *Jul. 4, 2017

(54) MUCOUS MEMBRANE ACTIVE AGENT APPLICATION

(71) Applicant: Andrew L. Skigen, Jacksonville, FL (US)

(72) Inventor: Andrew L. Skigen, Jacksonville, FL (US)

(*) Notice: Subject to any disclaimer, the term of this patent is extended or adjusted under 35 U.S.C. 154(b) by 178 days.

This patent is subject to a terminal disclaimer.

(21) Appl. No.: 14/307,959

(22) Filed: Jun. 18, 2014

(65) Prior Publication Data

US 2014/0301954 A1    Oct. 9, 2014

Related U.S. Application Data

(63) Continuation-in-part of application No. 13/732,408, filed on Jan. 1, 2013, now Pat. No. 9,192,572.

(60) Provisional application No. 61/582,453, filed on Jan. 2, 2012, provisional application No. 61/844,931, filed on Jul. 11, 2013.

(51) Int. Cl.
*A61K 9/70* (2006.01)
*A61K 31/245* (2006.01)
*A61K 9/00* (2006.01)

(52) U.S. Cl.
CPC ............ *A61K 9/7007* (2013.01); *A61K 9/006* (2013.01); *A61K 9/0056* (2013.01); *A61K 31/245* (2013.01); *A61K 9/0034* (2013.01)

(58) Field of Classification Search
CPC .... A61K 9/0056; A61K 9/0034; A61K 9/006; A61K 49/006; A61K 31/167; A61K 31/245; A61K 9/7007
See application file for complete search history.

(56) References Cited

U.S. PATENT DOCUMENTS

| 4,529,601 | A | * | 7/1985 | Broberg | ............... A61K 31/165 424/47 |
| 5,466,465 | A | * | 11/1995 | Royds | .................... A61K 9/703 424/447 |
| 6,620,852 | B2 | * | 9/2003 | Brogan | .................. A61K 31/00 514/535 |
| 2005/0014823 | A1 | * | 1/2005 | Soderlund | ............ A61K 9/0014 514/536 |
| 2006/0099550 | A1 | * | 5/2006 | Faasse | ................. A61C 19/063 433/215 |

FOREIGN PATENT DOCUMENTS

WO    WO 2005/018323    *    3/2005

* cited by examiner

*Primary Examiner* — Suzanne Ziska
(74) *Attorney, Agent, or Firm* — Joseph P. Kincart (57) ABSTRACT

The present invention provides methods of administering an active agent to a specifically identified area of mucous membrane of a human being, as well as a body dissolving film formed therefore.

21 Claims, 10 Drawing Sheets

MUCOUS MEMBRANE ACTIVE AGENT APPLICATION

CROSS REFERENCE TO RELATED APPLICATIONS

The present application claims priority to U.S. patent application Ser. No. 13/732,408 entitled: Oral Anesthesia Application, and filed Jan. 1, 2013, as a Continuation in Part Application; which in turn claims priority as a non-provisional conversion of U.S. Provisional Application Ser. No. 61/582,453 entitled Oral Anesthesia Application and filed Jan. 2, 2012 the contents of which are relied upon and incorporated herein by reference. The present application also claims priority to U.S. Provisional Application Ser. No. 61/844,931 entitled Mucous Membrane Active Agent Application, and filed Jul. 11, 2013, as a non-provisional conversion.

FIELD OF THE INVENTION

The present invention relates to methods and apparatus for topically applying medicaments to a mucous membrane. More specifically, the present invention presents methods and apparatus for providing one or more active agents to the human mucous membrane in a pain free fashion via adhesion of a film.

BACKGROUND OF THE INVENTION

The human body includes several areas of mucous membranes, including, without limitation, the oral cavity, the nasal cavities, the vaginal cavity and the anal cavity. Each of these areas is generally considered sensitive to pain. Therefore human beings tend to resist any procedures that interact with the mucous membranes. For example, it is estimated that as many as 75% of US adults experience some degree of dental fear, from mild to severe. It is further estimated that some 5 to 10 percent of U.S. adult dental patients are considered to experience dental phobia wherein they become so fearful of receiving dental treatment that they avoid dental procedures until they have a dental emergency, such as a toothache or dental abscess. Similarly, women tend to report apprehension about procedures that involve the vaginal area. In addition, people tend to report being more fearful of more invasive procedures which require anesthesia in order to manage pain, than they are of less painful treatments. The sensitive nature of most mucous membrane tissue promotes such fear.

What is needed therefore is a way to easily administer active agents, such as a medicament to a mucous membrane in a manner that causes little or no pain. Decreasing pain associated with mucous membranes will in turn lessen the apprehension associated with procedures involving the membranes.

SUMMARY OF THE INVENTION

Accordingly, the present invention provides methods and products for administering active agents to a human being via a mucous membrane. In particular, oral thin films are sized and shaped to adhere to areas of a mammalian reproductive area membrane and release an active agent to the area of the reproductive area membrane to which the dissolving film is adhered. The dissolving thin films may include, for example, body (BFDF") fluid dissolving films which provide quick release of an active pharmaceutical ingredient (API) when placed on a moist mucosal surface. Placing an active pharmaceutical ingredient into a dissolving thin film strip will make giving the human medication easier. The hydrophilic nature of the dissolving thin film strip makes it "stick" to a wet surface. Examples of these include: Oral mucosa, tongue, moist food. Once the medication is adhered, the human membrane will be exposed to the active agent and absorb it. In some embodiments, the film may dissolve completely via interaction with bodily fluids.

The present invention also provides methods and products for painlessly administering anesthetic agents in very specific topical areas of a mucous membrane. In particular, thin films including an anesthetic agent are sized and shaped to adhere to areas of a mammalian mucous membrane and release an anesthetic agent to the area of the membrane to which they are adhered. The thin films may include, for example, fluid dissolving films (b) which provide quick release of an active pharmaceutical ingredient (API) when placed on a moist mucosal surface.

The present invention provides for rapid adherence of the film to mucosal tissue and direct administration of an anesthetic agent directly to the site of adherence. In general, the film is placed on a mucosal tissue and hydrated with a body fluid; the body fluid hydration promotes adherent forces to bind the specifically sized BFDF on to a site of anesthetic application, or other delivery of an active agent. The anesthesia or other active agent is administered directly onto the adhesion site on the gum.

As the BFDF dissolves, traditional local anesthesia, such as an injection of additional medicaments, a surgery or other medical procedure may be administered directly into the mucosal membrane site that has been anesthetized by the anesthetic agent of the BFDF.

One general aspect includes a method of applying an active agent to a specific site on a human patient's mucous membrane, the method may include the steps of: selecting a body fluid dissolving film including an active agent; identifying an area for treatment on the human patient's mucous membrane for treatment by the active agent; placing the body fluid dissolving film including an active agent on the area for treatment; and treating the area for treatment with the active agent included in the body fluid dissolving film, where the treating the area for treatment includes an injection or incision to the mucous membrane.

Implementations may include one or more of features. For example, implementations may include the method where the area for treatment includes tissue within a mucous membrane. Implementations may additionally include the step of performing a medical procedure on the patient. The method may additionally include the step of administering an injection into the identified area for treatment. Further implementation may include the method where the active agent includes a topical anesthetic and the injection includes administration of an additional anesthetic. In some implementations, the method may include steps where the active agent includes ethyl ester of p-aminobenzoic acid. The method may include steps where the active agent includes benzocaine. The method may include steps where the active agent includes one or more of: butamben, dibucaine, lidocaine, oxybuprocaine, pramoxine, proparacaine, tetracaine and proxymetacaine. The method may additionally include the step of removing tissue from the area for treatment for treatment. Further implementation may include the method where the active agent includes a vitamin. The method may include steps where the active agent includes a nutraceutical. The method may include steps where the active agent includes a nutrient. The method may include steps where the active agent includes one or more of: an anti-fungal agent, an antimicrobial agent and an antibacterial agent.

Still further implementation may include the method where the body fluid dissolving film additionally includes a coloring agent and the method additionally includes the steps of: coloring mucous membrane with the coloring agent, identifying an area treated by the active agent via the colored agent, and treating the area for treatment in further manners. In some of these implementations, the method may include steps where the further manners include treating the area for treatment includes an injection into the colored mucous membrane. The method may include steps where the further manners include treating the area for treatment includes a biopsy tissue included in the colored mucous membrane. The method may include steps where the coloring agent includes one or more pigments derived from natural sources including one or more of: vegetables, minerals and animals. The method may include steps where the coloring agent includes one or more of: annatto, beet extract, caramel, beta-carotene and grape skin extract. Further implementations may include the method where the coloring agent includes one or more artificial colorings.

DETAILED DESCRIPTION

The present invention provides methods and products for locally administering one or more active agents to a human mucous membrane. The methods and products locally administer one or more active agents via adhesion of a film to the mucous membrane such as, for example, mucous membrane included in a human reproductive membrane area. A dissolving film containing an active agent is placed upon a mucous membrane, such as a membrane within the reproductive region. A hydrophilic nature of the dissolving film causes the film to stick to the mucous membrane. As the film dissolves, the active agent may be absorbed through the skin of the mucous membrane.

According to various embodiments of the present invention, the active agent may include, for example a medication for treating a condition present in the recipient or to prophylactically treat the patient. The active agent may include, for example an anesthetic. Some specific examples include an active agent including ethyl ester of p-amino benzoic acid (PABA), such as, for example, benzocaine. Other examples may include, but are not limited to: benzocaine, butamben, dibucaine, lidocaine, oxybuprocaine, pramoxine, proparacaine, proxymetacaine, and tetracaine (also named amethocaine). In general, according to the present invention, a film with an active agent is placed upon a mucous membrane and an area of the mucous membrane is anesthetized such that a procedure, such as an injection, may be administered to the anesthetized area.

As discussed more fully below, other exemplary areas of mammalian mucous membrane may include, but not be limited to a mammalian vaginal cavity, a nasal passage and a rectal cavity. Other procedures may include a biopsy or other minor incision. A biopsy or incision may include, by way of example a cervical biopsy which may be painful without anesthesia.

GLOSSARY

Body Fluid Dissolving Films (sometimes referred to herein as "BFDF") as used herein shall mean a non-toxic film which may be placed in contact with a mucous membrane and dissolve as a result of contact with saliva, body fluid or other liquid.

In various embodiments, BFDFs may contain, by way of teaching example one or more of: film-forming polymers such as hydroxypropylmethyl cellulose (HPMC), hydroxypropyl cellulose (HPC), pullulan, carboxymethyl cellulose (CMC), pectin, starch, polyvinyl acetate (PVA), and sodium alginate.

A BFDF according to the present invention may additionally include supplementary ingredients such as, by way of example: plasticizers, sweetening and flavoring agents, coloring agents, saliva-stimulating agents, and thickening agents. Inactive ingredients may include: Methocel K3, Methocek K100, Methocel K4, Sodium Carboxymethyl Cellulose, Glycerine, Sucralose, Polysorbate 80, Peppermint Oil Flavor, Gum Arabic, Sodium Copper Chlorophylin.

An active agent or a medicament includes a substance that promotes recovery from injury or ailment. Active agents may include a pharmaceutical; drug; nutraceutical or nutritional aid; vitamin, herb or other substance administered to promote health.

Body Cavity Based Size and Shape (sometimes referred to herein as "BCBSS") as used herein shall mean a size and shape of a BFDF suitable for placement on the surface of a mucous membrane and/or tissue or medical instrument for placement on a mucous membrane. A body cavity may include the oral cavity, the vaginal cavity and the anal cavity.

Figure 1:
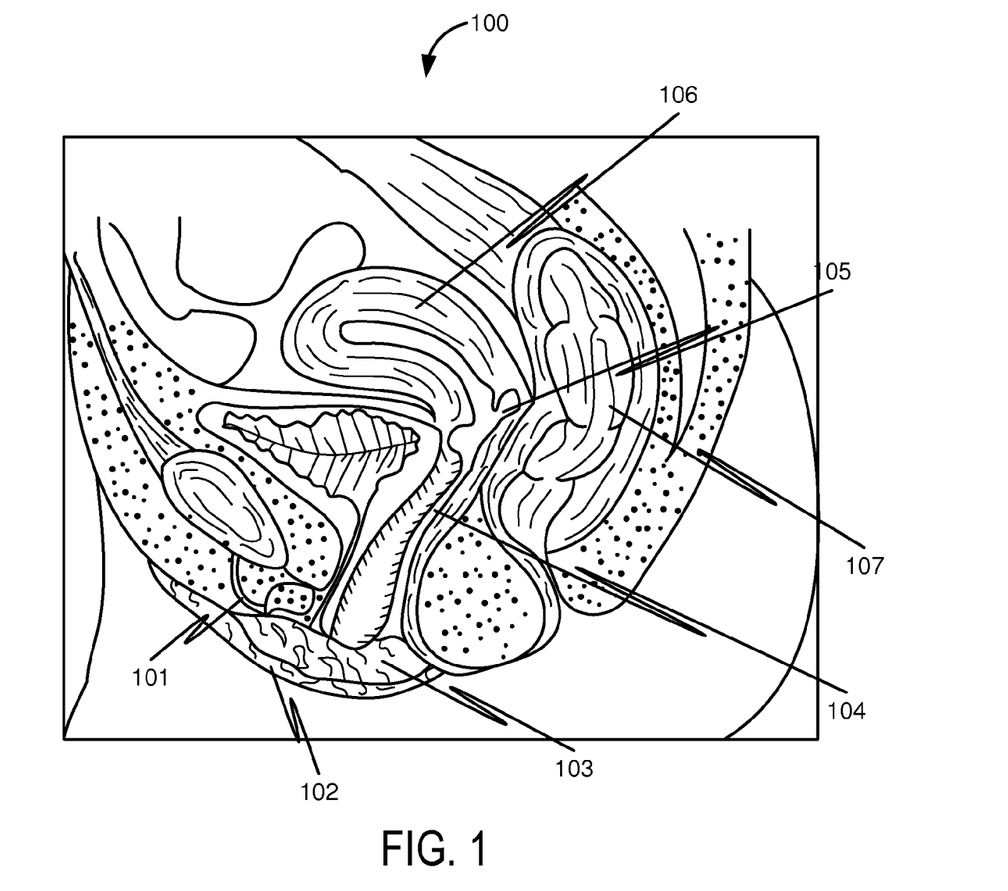
FIG. 1 illustrates an organ of the human female reproductive area which includes mucosal tissue with which the present invention may be implemented.

Referring now to FIG. 1, a cut away diagram 100 of a human reproductive area and anal area is illustrated. As presented, in order of presentation, several portions of the human female reproductive system include topical areas with mucosal tissue, sometimes referred to as mucous membrane. The clitoris 101, the Labia Majora 102, the Labia Minora 103, the vaginal wall 104 the cervix 105 and the uterus 106 all include mucous membrane tissue. In addition, as discussed more fully below, the anal region, and in particular the rectum 107 includes mucous membrane tissue. According to the present invention, a film including an active agent may be applied to the mucous of these areas 101-107.

Figure 2:
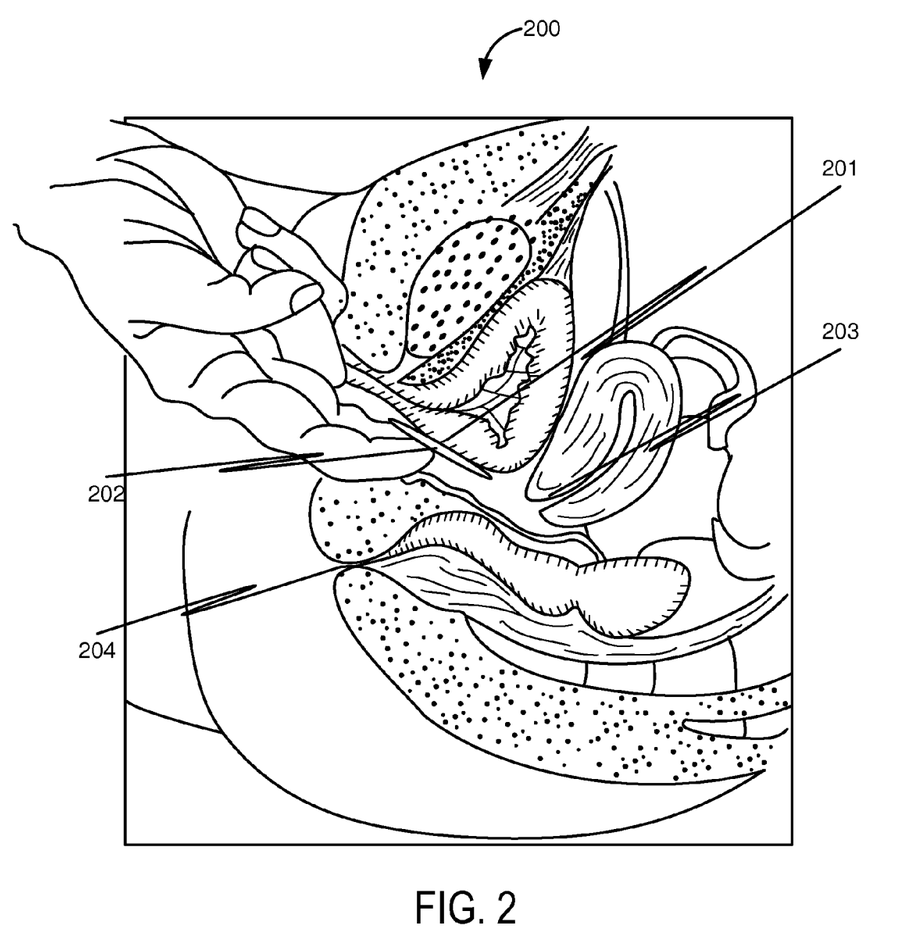
FIG. 2 illustrates administration of a BFDF strip in a mucous membrane according to some embodiments of the present invention.

Referring now to FIG. 2, 200, a cut away view of a BFDF 202 being applied to a mucous membrane 201 is illustrated. In the example illustrated, the mucous membrane 201 includes a vaginal wall. The uterus 203 and the rectum 204 may also receive a film with an active agent. As illustrated, the film is applied by placing the film on a finger and placed onto the tissue of the mucous membrane 201. A BFDF 202 may be placed with light pressure against the mucous membrane 201. The moisture of the mucous membrane 201 will cause the BFDF 202 to adhere to the mucous membrane 201. The BFDF 202 may be in various shapes, such as oval or rectangular shaped based upon the area of mucous membrane 201 to be treated.

Figure 3:
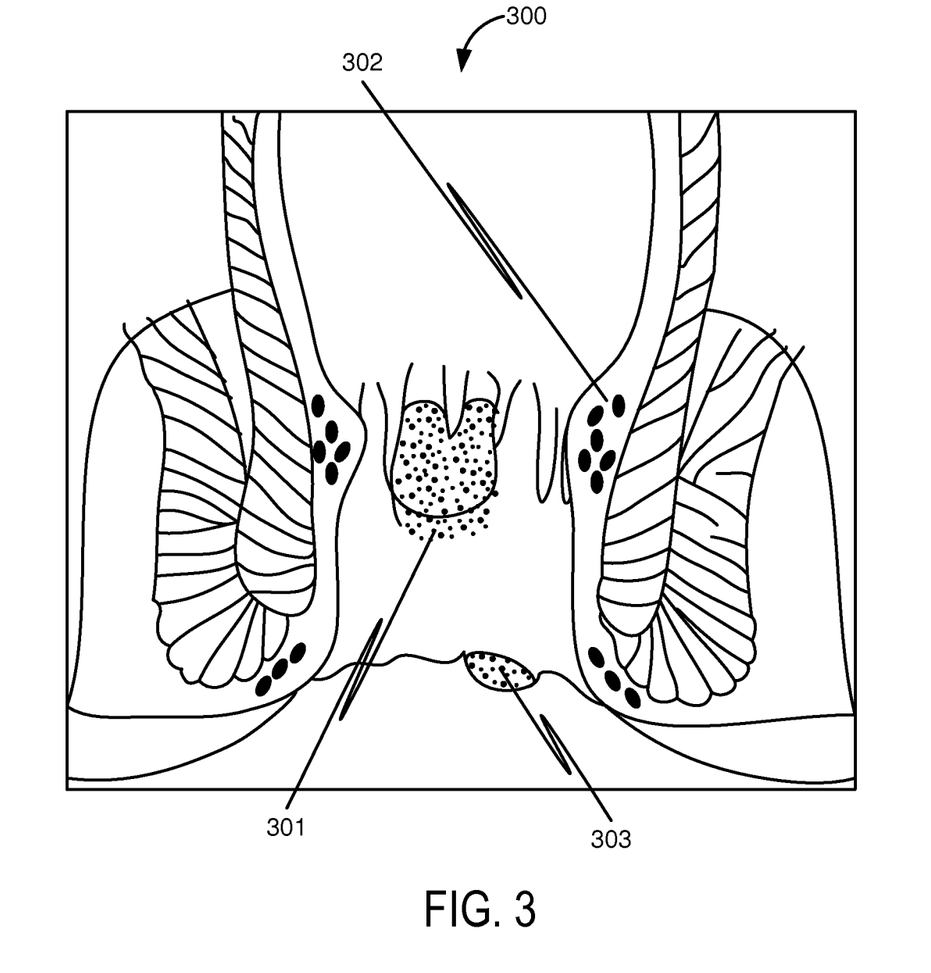
FIG. 3 illustrates additional mucous membrane areas for application of a BFDF according to some embodiments of the present invention.

Referring now to FIG. 3, 300, additional areas of mucous membrane 301-303 that may be treated by an active agent in a BFDF. For example, in FIG. 3, hemorrhoids and areas affected by hemorrhoids in the areas of mucous membranes 301-303 may be included as mucosal membranes that may be treated with an active agent in a BFDF.

Figure 4:
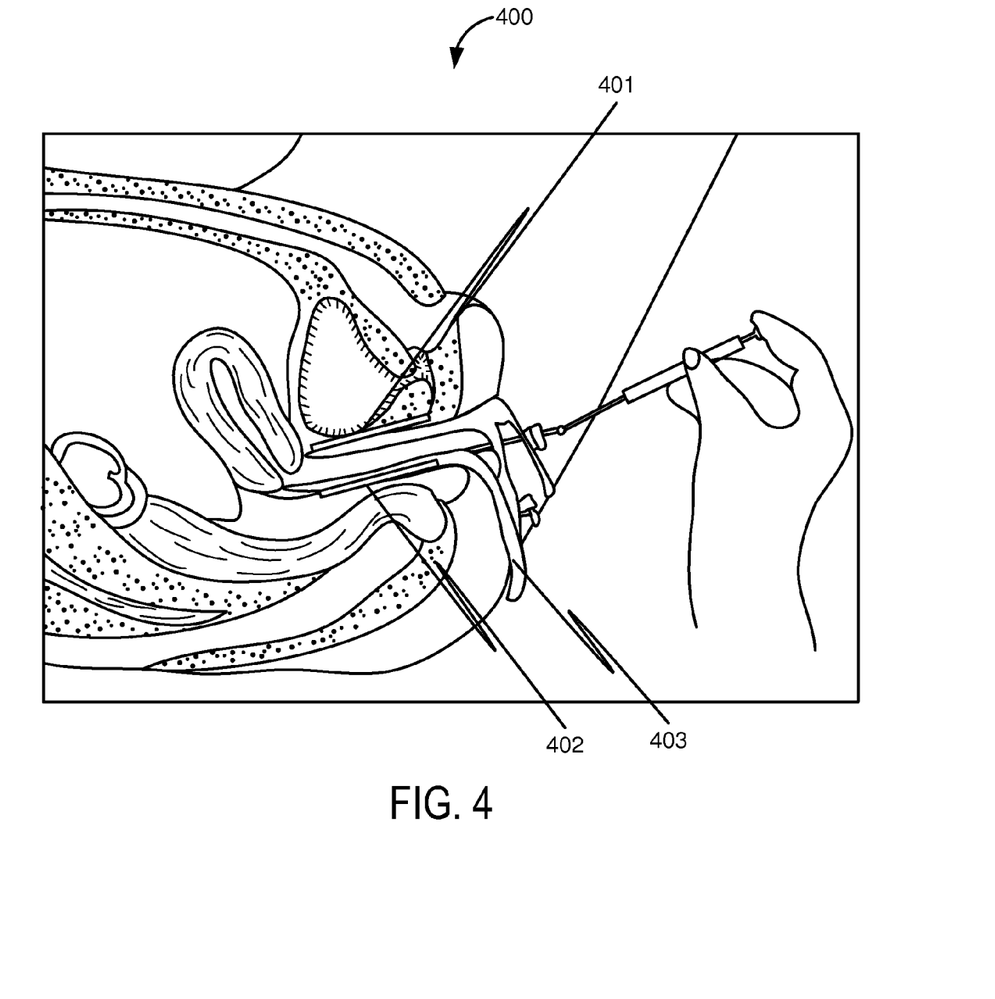
FIG. 4 illustrates application of a BFDF along a medical procedure device, according to some embodiments of the present invention.

Referring now to FIG. 4, 400, a medical procedure affecting mucosal membranes is illustrated. One example of a procedure that may be enhanced with a BFDF is a dilation and curettage, a surgical procedure that includes dilating or opening the cervix with a thin instrument and a thin instrument is inserted into the uterus. A D&C is used to diagnose and treat many conditions that may affect the uterus, such as abnormal bleeding. A D&C also may be conducted following a miscarriage. Tissue is removed from the cervix and/or surrounding area for examination under a microscope to look for abnormalities.

A cervix may be dilated using a laminaria, essentially a slender rod of natural or synthetic material that is inserted into the cervix. It is sometimes left in place for several hours. The rod absorbs fluid from the cervix and surrounding mucous membrane and swells. The swelling causes the cervix to open. According to the present invention, a film containing one or more active agents may coat the laminaria or otherwise be administered to the area where the laminaria will be placed. The active agents may include an anesthetic and/or antibiotic to treat the affected areas.

During a D&C a speculum 402 may also be inserted into the vagina to open the vagina and allow access to the cervix. According to the present invention, a BFDF 401-402 containing one or more active agents may also be placed upon the speculum on those parts of the speculum that will come into contact with the vagina or other mucous membrane. The speculum 403 is included by way of example, other instruments may also be used in conjunction with the present invention. As indicated above, the BFDF may contain one or more active agents, such as an anesthetic, an anti-inflammatory, and an antibiotic.

Figure 5:
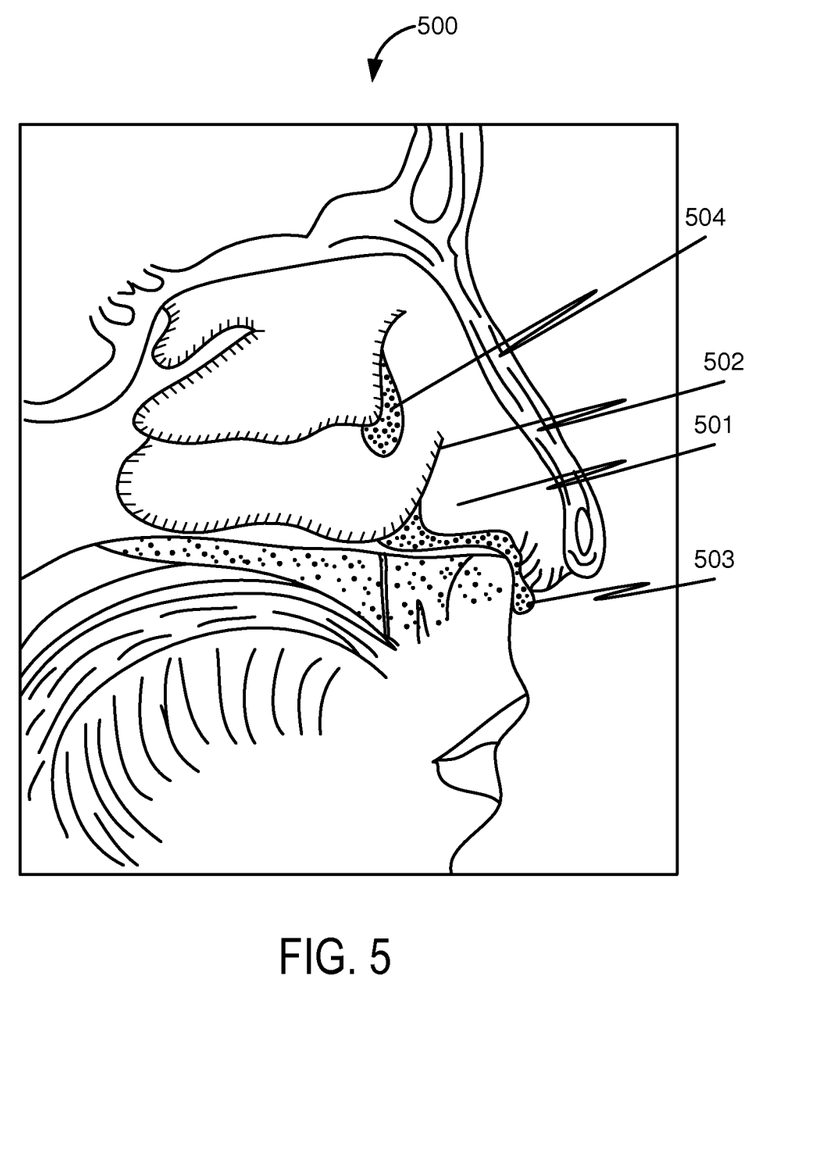
FIGS. 5-6 illustrate additional mucous membrane areas including the nasal passage for application of a BFDF according to some embodiments of the present invention.

Referring no to FIG. 5, a cutaway of a nasal cavity 500 is illustrated. A BFDF 501 may be adhered to tissue within the nasal cavity 500. In some embodiments, the BFDF may include an active agent that will treat a condition associated with the nasal cavity, such as one or more of" inflammation 502; nasal discharge 503 and a polyp 504. In other embodiments, the BFDF 501 will include an active agent that will be absorbed through normal mucous membrane in the nasal cavity and be absorbed for systemic treatment.

Figure 6:
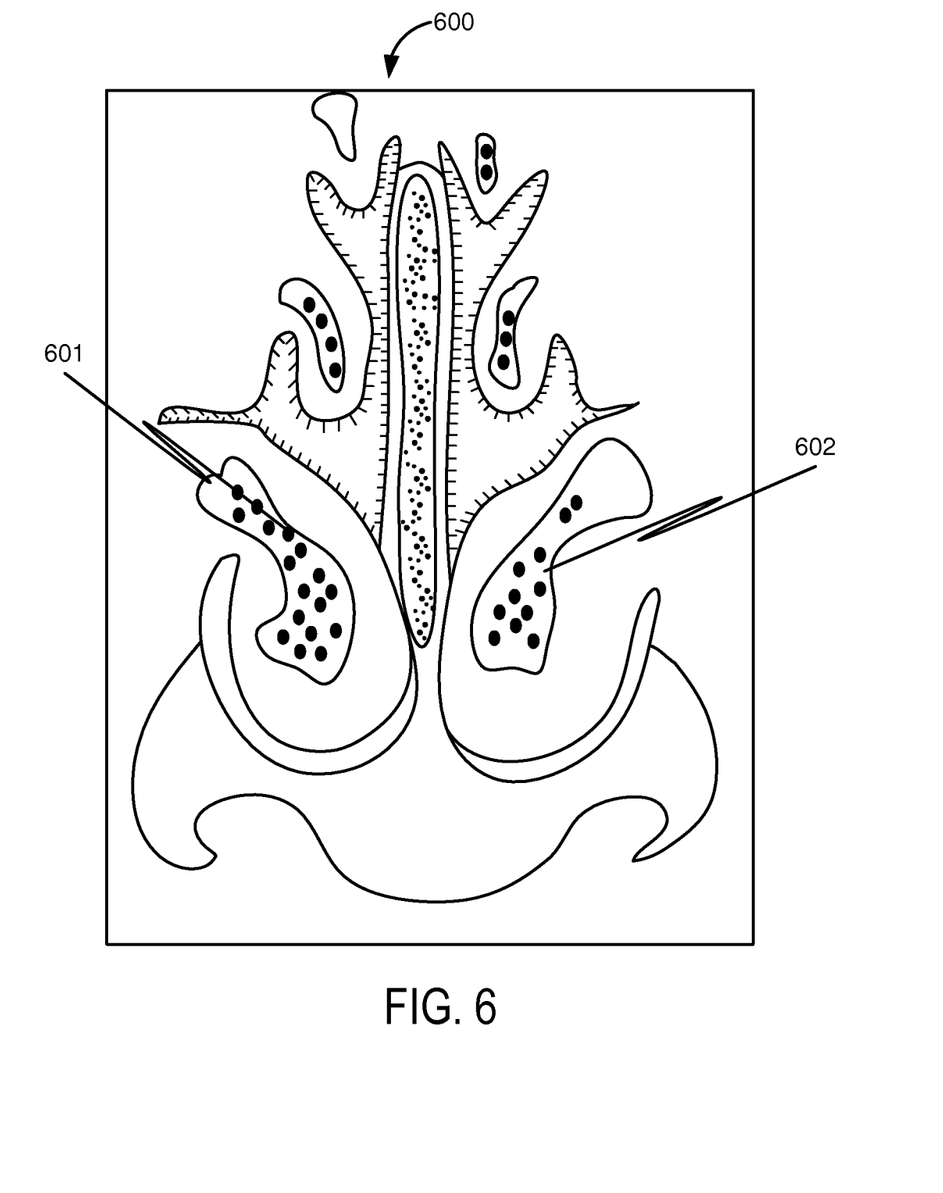

Referring now to FIG. 6, a cut away illustration of a nasal area 600 following a surgery is shown. In the surgery being illustrated, a portion of bone 601 is removed from the nasal area 600. According to the present invention, a BFDF 602 may be applied to the nasal areas affected and an active agent may treat the affected areas in the nasal area 600.

Figure 7:
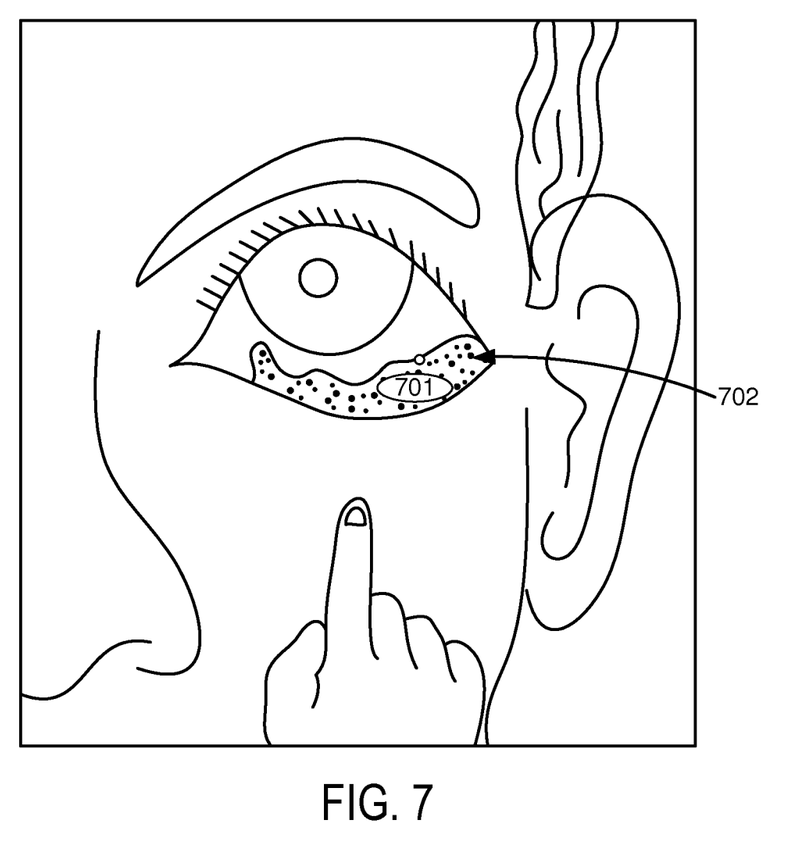
FIG. 7 illustrates a mucous membrane area including ophthalmic tissue according to some embodiments of the present invention

Referring now FIG. 7, another area that a BFDF 701 may be applied is in the ocular region 702 with moist tissue. A BFDF 701 in the ocular region 702 may include an active agent for addressing dry eye, an anti-inflammatory, an antibiotic, a vitamin, a supplement, a nutraceutical, or other agent.

In embodiments manifesting an inflammation, such as mucous membrane pemphigoid (MMP), a chronic systemic autoimmune blistering disease that affects any mucous membrane may be treated. MMP may be characterized by linear deposition of IgG, IgM, IgA or C3 along the epithelial basement membrane that leads in most mucosal tissue to progressive scar formation. Typically, MMP affects older people and the adhesive qualities of a BFDF may help the BFDF stay in place during ocular movement.

Patients with ocular manifestations of MMP often present with a nonspecific chronic conjunctivitis, with symptoms consisting of irritation, burning and tearing. MMP may worsen into progressive sub epithelial fibrosis of the conjunctiva with subtle blunting of the fornix to frank symblepharon formation, shrinkage and obliteration of the conjunctival fornices (FIG. 2). Conjunctival scarring may lead to trichiasis and further progress to cicatricial entropion with trichiasis.

In some cased, conjunctival scarring may be accompanied by obliteration of the lacrimal ductules and accessory glands and goblet cells, which in turn may cause dry eye symptoms secondary to aqueous tear deficiency and evaporative tear dysfunction.

Blisters or bullae in subepithelial location may also be used to characterize MMP. Tissue adjacent to a blister may also be affected, due to tissue-fixed immunoglobulins within the blister that have been destroyed by inflammatory infiltrate.

Medical treatment of MMP involving the ocular surface may be aggressive to prevent further damage due to keratoconjunctival sicca and advanced cicatricializing disease leading to ankyloblepharon. MMP is a systemic disease, but topical therapy is often a part of a therapy. And BFDF administered in the ocular region may assist in maintaining consistent and effective administration of an active agent.

Topical treatment may be accompanied by systemic treatment, such as, for example, treatment with prednisone and cyclophosphamide or azathioprine. For less progressive disease, dapsone (50 mg to 200 mg per day) can be considered as an alternative initial therapy.

A BFDF may assist in the production of tears. A secondary bacterial infection may be treated based on culture and sensitivity. In some embodiments, the secondary bacterial infection may include a topical antibiotic administered via the BFDF.

Figure 8:
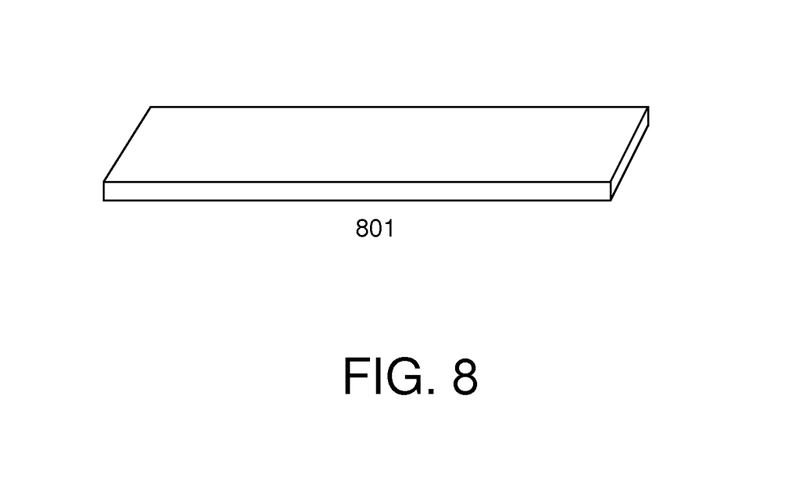
FIG. 8-9 illustrates rectangular shape and oval shape implementations of a BFDF according to some embodiments of the present invention.
Figure 9:
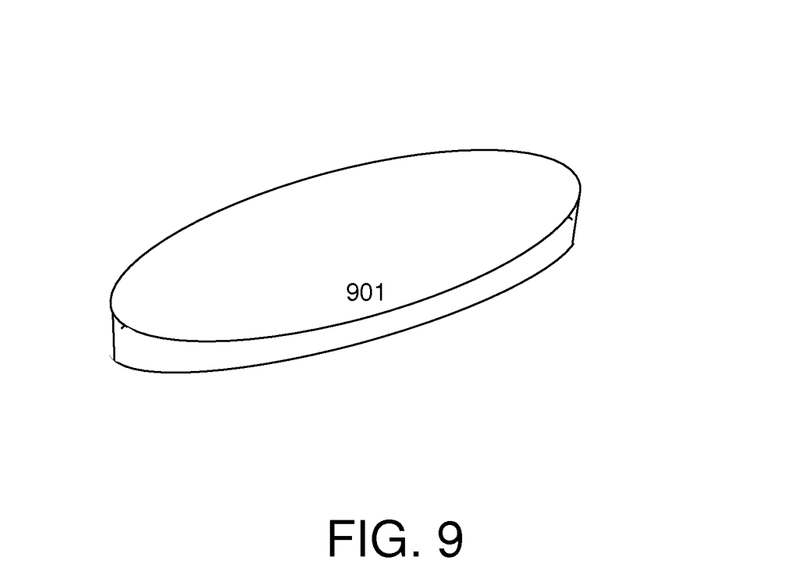

Referring now FIG. 8 and FIG. 9, perspective views of exemplary shapes of Oral Cavity Based Shapes are illustrated. Illustrated shapes include, by way of example, rectangular 801 and oval shapes 901. Other shapes are also within the scope of the present invention. In some embodiments, a BFDF may be one or both of: shaped and sized with a scissor prior to placement on a mucous membrane. Placement may be accomplished via a human finger or a swab or other instrument. As discussed above, placement on a tool or other device which will come into contact with mucous membrane is also within the scope of this invention. In some examples, the BFDF 801-901 may be adhered to the tool with an adhesive layer between the tool and the BFDF 801-901.

Figure 10:
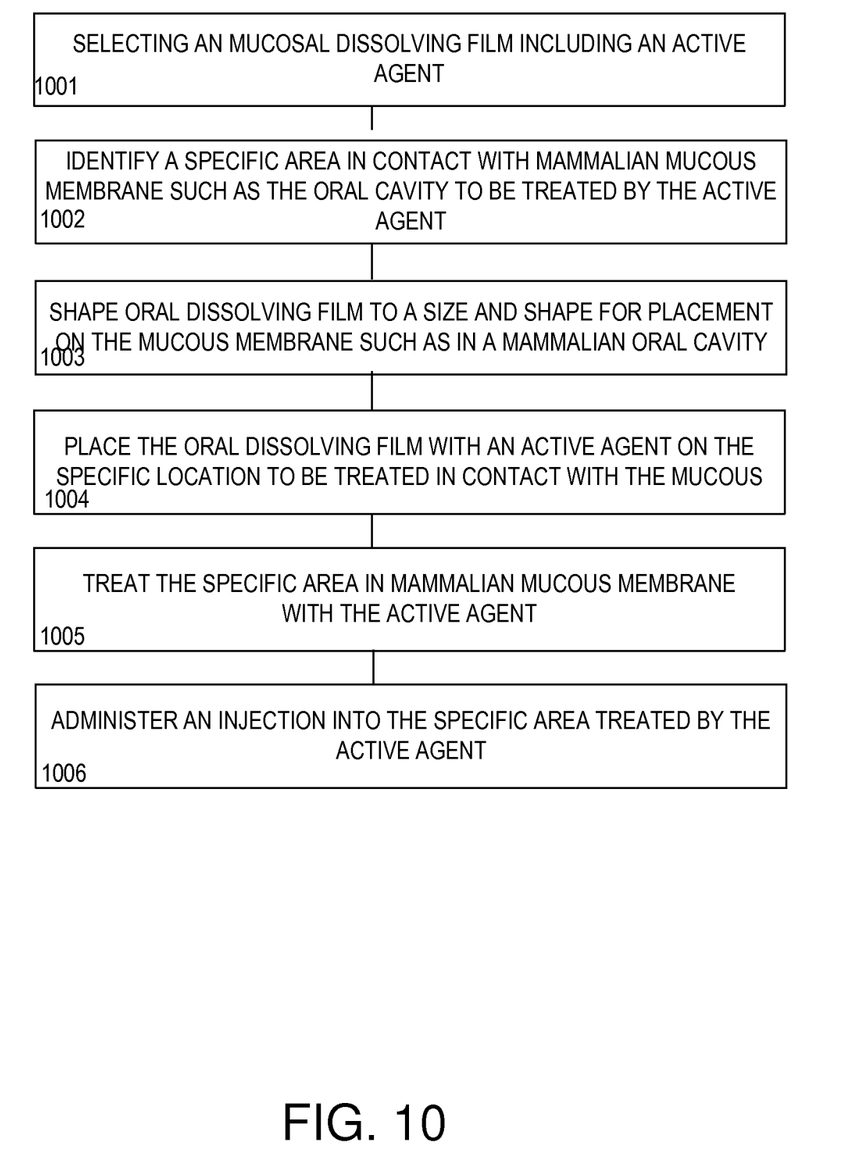
FIG. 10 illustrates method steps that may be practiced in some implementations of the present invention.

Referring now to FIG. 10, exemplary steps that may be practiced in some embodiments of the present invention are illustrated. The steps are presented in a logical order for some embodiments, however, the order presented is by way of example only and not meant to limit the scope of the invention. At 1001, an active agent may be included in a BFDF. At 1002, a specific location or area of mucous membrane to be anesthetized or otherwise treated by an active agent included within the BFDF. At 1003, the BFDF may be sized and shaped such that it is suitable for placement on the specific location or area identified. At 1004, the BFDF which has been shaped is placed at the desired location to be treated. At 1005, the specific location or area in the mucous membrane which be treated received the effect of the active agent.

At 1006, an injection or other medical procedure, such as a biopsy or other tissue incision or tissue removal may be administered into the specified area. In some embodiments, an injection may include additional anesthesia.

In some embodiments, the BFDF includes an active agent which includes a pharmaceutical ingredient. The pharmaceutical ingredient may be absorbed at the specified location for local oral administration as opposed to systemic active pharmaceutical ingredient.

According to some embodiments, the active pharmaceutical ingredients may include those known to topically treat membrane conditions such as, by way of non-limiting example, one or more of: anesthetics, anti-bacterials, anti-inflammatory agents, antifungals; antiseptics; and topical steroids.

According to the present invention, the nature of the film that is included in the BFDF fixates the location of active pharmaceutical ingredient, eliminating migration, dissipation and dilution. The adhesion may be described as mucoadherence, wherein muco-adherence allows for a lower concentration of a given active pharmaceutical ingredient to be used to achieve a desired amount of anesthetic action and/or a desired health benefit.

Generally, lower concentration of an active agent may be beneficial due to a decrease in deleterious systemic side effects of excessive active pharmaceutical ingredient absorption such as methemaglobinemia or excessive exogenous steroids.

In some embodiments, and BFDF may include a coloring agent to provide a visual indication of when the BFDF dissolves and also a visual indication of which of the oral mucosa has been treated for easier identification of a treated area. Coloring agents may include, for example, a substance that allows a practitioner to identify an area that has been treated by an active agent, such as an anesthetic, whereby an injection may be administered into the area that has been made numb by anesthetic.

Coloring agents may include any benign coloring that is visible to a practitioner who will administer an injection. Accordingly, coloring agents may include by way of non-limiting example, natural pigments derived from natural sources such as vegetables, minerals or animals. Including: annatto, beet extract, caramel, beta-carotene and grape skin extract.

Other examples of coloring agents may include: Caramel coloring (E150), or other coloring made from caramelized sugar; Annatto (E160b), a reddish-orange dye or other coloring made from the seed of the achiote; Chlorophyllin (E140), a green dye or other coloring made from *chlorella* algae; Cochineal (E120), a red dye or other coloring derived from the cochineal insect, *Dactylopius coccus*; Betanin (E162) or other coloring extracted from beets; Turmeric or other coloring derived from curcuminoids, E100; Saffron or other coloring derived from carotenoids, E160a; Paprika (E160c); Lycopene (E160d); Elderberry juice; Pandan a green coloring or other coloring derived *Pandanus amaryllifolius*; Butterfly pea a blue dye or other coloring derived from *Clitoria ternatea*.

Other Coloring agents may include coloring approved under the Pure Food and Drug Act including, but not limited to: FD&C Blue No. 1—Brilliant Blue FCF, E133 (blue shade); FD&C Blue No. 2—Indigotine, E132 (indigo shade); FD&C Green No. 3—Fast Green FCF, E143 (turquoise shade); FD&C Red No. 40—Allura Red AC, E129 (red shade); FD&C Red No. 3—Erythrosine, E127 (pink shade, commonly used in glacé cherries); FD&C Yellow No. 5—Tartrazine, E102 (yellow shade); and FD&C Yellow No. 6—Sunset Yellow FCF, E110 (orange shade).

In some preferred embodiments, the BFDF with an active agent includes a film that is colored, so that when the BFDF dissolves, the treated oral mucosa is easily identified.

The BFDF may also be stored in aseptic packaging, limiting cross contamination and include flavoring which is pleasant to taste.

In some embodiments, exemplary BFDFs may contain film-forming polymers such as hydroxypropylmethyl cellulose (HPMC), hydroxypropyl cellulose (HPC), pullulan, carboxymethyl cellulose (CMC), pectin, starch, polyvinyl acetate (PVA), and sodium alginate.

Additional ingredients that may be included in various embodiments include one or more of: plasticizers, sweetening and flavoring agents, coloring agents, saliva-stimulating agents, and thickening agents. In some preferred embodiments, inactive ingredients may include: Methocel K3, Methocek K100, Methocel K4, Sodium Carboxymethyl Cellulose, Glycerine, Sucralose, Polysorbate 80, Peppermint Oil Flavor, Gum Arabic, and Sodium Copper Chlorophylin.

Active agents may also include, for example a vitamin treatment, a nutraceutical, a nutrient, an antimicrobial or antibacterial agent. In some embodiments, an active agent may include an anesthetic that is administered prior to an injection, a biopsy or other medical procedure such as an incision. Specific examples include an active agent including ethyl ester of p-amino benzoic acid (PABA), such as, for example, benzocaine. Other examples may include, but are not limited to: benzocaine, butamben, dibucaine, lidocaine, oxybuprocaine, pramoxine, proparacaine, proxymetacaine, and tetracaine (also named amethocaine). A film with an active anesthetic agent is placed upon a mucous membrane and an area of the mucous membrane is anesthetized such that a procedure, including for example as an injection or an incision, may be administered to the anesthetized area.

In another aspect of the present invention, the BFDF, may be stored in aseptic packing to limit cross contamination. The BFDF may also be individually labeled to identify the contents and dosage.

Figure 11:
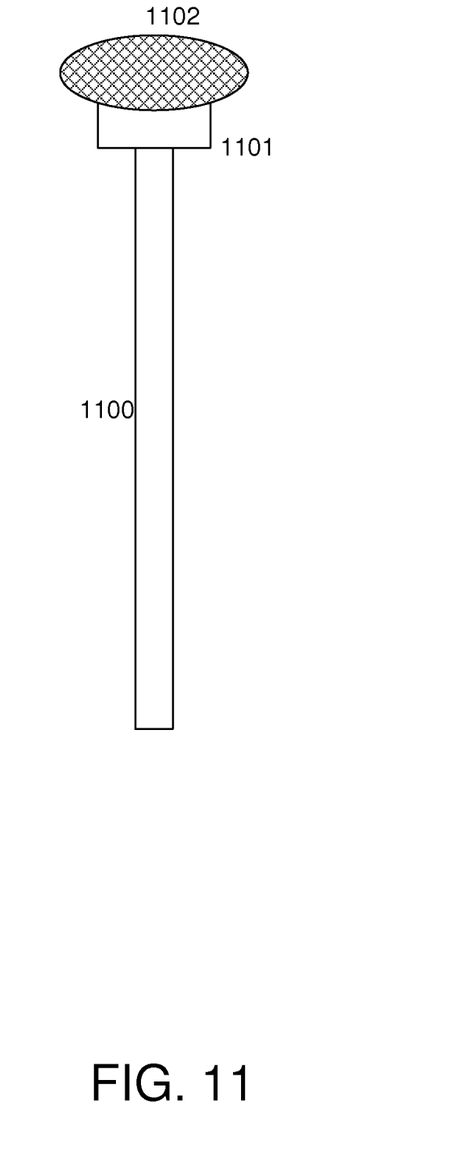
FIG. 11 illustrates an applicator that may be used in some implementations of the present invention.

Referring now to FIG. 11, in some embodiments, an applicator 1100 may also be used to assist in placing the BFDF 1102 within an area of mucous membrane with limited access. The BFDF 1102 may be mounted on an application pad 1101 and applied by swiping the BFDF 1102 over an area of the oral cavity that is moist. Aseptic packaging may enclose all of, or some portions of the entire applicator 1100, including application pad 1101 and BFDF 1102, the application pad 1101 and BFDF 1102, or just the BFDF 1102.

An aseptic package may also be labeled to identify dosage and side effects of any active agents included within the BFDF 1102. In some embodiments, the BFDF 1102 itself may be printed upon to identify the active agent and dosage information.

In still other embodiments, a film with an active agent may be placed upon a mucous membrane and an area of the mucous membrane is anesthetized so that a procedure, such as an injection or an incision, may be administered to the anesthetized area.

EXAMPLES

In vitro and in vivo studies were conducted to gauge the effectiveness of a novel oral mucosa adhesive, moderately water-soluble, pliant polymer artificial dentifrice (AD) film containing dibucaine (DC) for relief of pain due to oral erosion. The film was prepared from a hydroxypropyl cellulose-M (HPC-M) ethanol solution containing varying amounts of DC, as well as polyethylene glycol.

In the in vitro experiments, the disintegration of HPC-M showed a lag time of about 50 min, a much lower rate than that of drug release, which more or less leveled off after 50 min. Twenty-five percent of the DC was released from the film (0.113 and 0.225 mg/cm2) after the initial 5 min, which then reached about 80% after 50 min, the time at which the polymer began to break up. In the in vivo study, the local anesthetic effect of the film was evaluated in 23 patients (10 males, 13 females) suffering from the adverse effects of chemotherapy. When applied to the wet surface of the mucosa, the AD film absorbed moisture and showed excellent adhesion. Pain relief in patients lasted 2.2+/−0.21 and 4.3+/−0.25 h at DC doses of 0.113 and 0.225 mg/cm2, respectively. These results suggest that the AD film may cover mucositis sites of oral mucosa long enough to allow DC release and bring relief from pain arising from chemotherapy and/or radiotherapy.

2. Pediatric Dent. 2001 January-February; 23(1):11-4.

Comparison of topical EMLA 5% oral adhesive to benzocaine 20% on the pain experienced during palatal anesthetic infiltration in children.

Primosch R E, Rolland-Asensi G.

Department of Pediatric Dentistry, University of Florida College of Dentistry, Gainesville, Fla., USA. rprimosch@dental.ufl.edu Example 1

PURPOSE: The purpose of this investigation was to compare the pain responses of children during local anesthetic infiltration at bilateral palatal sites prepared with the topical application of benzocaine 20% oral adhesive (Orabase-B) versus benzocaine 20% gel (Hurricaine) or EMLA 5% oral adhesive (EMLA 5% cream in Orabase Plain).

METHODS: Forty subjects, aged 7-15 years old, received bilateral palatal injections following topical application of anesthetic agents applied in a randomized, crossover design. Pain responses were compared based upon subject self-report using a visual analogue scale (VAS), changes in the subject's heart rate, and operator assessment using a modified Children's Hospital of Eastern Ontario Pain Scale (CPS) that rated behavioral changes in children. Following the injections, the subjects were asked to choose which agent was preferred based on comfort and taste acceptance.

RESULTS: All the agents tested were equivalent in injection pain response comparisons, but Hurricaine had a slight advantage in expressed subject preference and taste acceptance over the other topical anesthetic agents tested.

Example 2

Clinical evaluation of MGI 209, an anesthetic, film-forming agent for relief from painful oral ulcers associated with chemotherapy.

LeVeque F G, Parzuchowski J B, Farinacci G C, Redding S W, Rodu B, Johnson J T, Ferretti G A, Eisenberg P D, Zimmer M B.

Harper Hospital, Detroit, Mich. 48201.

PURPOSE: This open-label, multicenter trial evaluated the efficacy of a muco-adherent, anesthetic medication, (MGI 209) for relief from painful oral ulcers associated with cytotoxic chemotherapy.

PATIENTS AND METHODS: Twenty-eight eligible cancer patients who had up to five discrete oral ulcers (total area<or =5 cm2) completed this study. Mean age was 53.5 years (range, 21 to 81). Subjective assessments of oral discomfort before and after an orange juice pain challenge (OJPC), which was measured using a visual analog scale (VAS), and visual estimates of the amount of MGI 209 that remained on treated ulcers were collected at (1) baseline (before MGI 209 treatment); and (2) 30, 60, 120, and 180 minutes post treatment.

RESULTS: Most subjects had low VAS scores (4 or less), which was indicative of oral discomfort, at baseline before and after the OJPC. At 30, 60, 120, and 180 minutes after MGI 209 treatment, most subjects had high VAS scores before and after an OJPC compared with baseline scores, which was indicative of a substantial increase in oral comfort; these differences were statistically significant ($P<0.0001$). Mean percent of MGI 209 estimated to remain on ulcers at the previously mentioned times was 93.7%, 90.3%, 79.6%, and 71.3% of the total amount applied, respectively.

Example Conclusion: Benzocaine hydrochloride in combination with the protective, muco-adherent film-coating relieved discomfort for at least 3 hours even with exposure to an irritating beverage. MGI 209 treatment should allow patients with chemotherapy-induced oral ulcers to drink and eat with significantly diminished pain or no pain.

CONCLUSION

The present invention, as described above and as further defined by the claims below, provides methods of administering an active agent to a localized mucous membrane of a mammal, as well as a BFDF formed therefore. The exemplary style of describing the present invention is not meant to limit the scope of the invention and the invention is therefore more clearly described and limited by the claims below.

What is claimed is:

1. A method of applying an active agent to a specific site on a human patient's mucous membrane, the method comprising the steps of:

selecting a body fluid dissolving film comprising an active agent comprising a local anesthetic active agent and a coloring agent;

identifying an area for treatment on the human patient's mucous membrane comprising a human reproductive organ area tissue for treatment by the active agent;

placing the body fluid dissolving film comprising an active agent on the area for treatment;

anesthetizing the identified area with the local anesthetic active agent and coloring the identified area with the coloring agent;

dissolving the dissolving film essentially in its entirety;

generating a visual indicator on the identified area of the mucous membrane with the coloring agent, wherein the visual indicator remains on the mucous membrane following the dissolving of the dissolving film essentially in its entirety; and treating the identified with the visual indicator, wherein the treatment includes an injection or incision to the mucous membrane.

2. The method of claim 1 wherein the area for treatment comprises tissue within a vaginal cavity.

3. The method of claim 2 additionally comprising the step of performing a medical procedure on the patient.

4. The method of claim 3 additionally comprising the step of administering an injection into identified area for treatment.

5. The method of claim 3 additionally comprising the step of removing tissue from the area for treatment.

6. The method of claim 4 wherein the active agent comprises a topical anesthetic and the injection comprises administration of an additional anesthetic.

7. The method of claim 6 wherein the active agent comprises ethyl ester of p-aminobenzoic acid.

8. The method of claim 6 wherein the active agent comprises tetracaine.

9. The method of claim 6 wherein the active agent comprises one or more of:
butamben, dibucaine, lidocaine, oxybuprocaine, pramoxine, proparacaine and proxymetacaine.

10. The method of claim 1, wherein the active agent comprises a vitamin.

11. The method of claim 1, wherein the active agent comprises a nutraceutical.

12. The method of claim 1, wherein the active agent comprises a nutrient.

13. The method of claim 1, wherein the active agent comprises one or more of: an anti-fungal agent, an antimicrobial agent and an antibacterial agent.

14. The method of claim 1 wherein the body fluid dissolving film additionally comprises a coloring agent and the method additionally comprises the steps of:
coloring mucous membrane with the coloring agent;
identifying an area treated by the active agent via the colored agent; and
treating the area for treatment in further manners.

15. The method of claim 14 wherein the further manners comprise treating the area for treatment comprises an injection into the colored mucous membrane.

16. The method of claim 14 wherein the further manners comprise treating the area for treatment comprises a biopsy tissue included in the colored mucous membrane.

17. The method of claim 14 wherein the coloring agent comprises one or more pigments derived from natural sources comprising one or more of: vegetables, minerals and animals.

18. The method of claim 14 wherein the coloring agent comprises one or more of: annatto, beet extract, caramel, beta-carotene and grape skin extract.

19. The method of claim 14 wherein the coloring agent comprises one or more of: Caramel coloring (E150); Annatto (E160b), coloring made from seeds of achiote; Chlorophyllin (E140); a green dye made from *chlorella* algae; Cochineal (E120), a red dye derived from cochineal insects; *Dactylopius coccus*; Betanin (E162); coloring extracted from beets; Turmeric coloring derived from curcuminoids; E100; coloring derived from carotenoids; E160a; Paprika (E160c); Lycopene (E160d); Elderberry juice; coloring derived *Pandanus amaryllifolius*; Butterfly pea a blue dye; and coloring derived from *Clitoria ternatea*.

20. The method of claim 14 wherein the coloring agent comprises one or more artificial colorings.

21. The method of claim 14 wherein the coloring agent comprises one or more of: FD&C Blue No. 1—Brilliant Blue FCF, E133 (blue shade); FD&C Blue No. 2—Indigotine, E132 (indigo shade); FD&C Green No. 3—Fast Green FCF, E143 (turquoise shade); FD&C Red No. 40—Allura Red AC, E129 (red shade); FD&C Red No. 3—Erythrosine, E127 (pink shade, commonly used in glacé cherries); FD&C Yellow No. 5—Tartrazine, E102 (yellow shade); and FD&C Yellow No. 6—Sunset Yellow FCF, E110.

* * * * *